United States Patent [19]

Bille et al.

[11] Patent Number: 4,732,473
[45] Date of Patent: Mar. 22, 1988

[54] APPARATUS FOR, AND METHODS OF, DETERMINING THE CHARACTERISTICS OF SEMI-CONDUCTOR WAFERS

[76] Inventors: Josef Bille, AM Pferchelhang 2/4; Siegfried Hunklinger, AM Buchsenackerhang 68, both of 6900 Heidelberg, Fed. Rep. of Germany

[21] Appl. No.: 742,531

[22] Filed: Jun. 7, 1985

[30] Foreign Application Priority Data

Jun. 14, 1984 [DE] Fed. Rep. of Germany ....... 3422143

[51] Int. Cl.$^4$ ........................................... G01N 21/88
[52] U.S. Cl. ..................................... 356/237; 250/560; 356/372
[58] Field of Search ................ 250/201, 560; 356/376, 356/381, 375, 237, 372

[56] References Cited

U.S. PATENT DOCUMENTS

| | | | |
|---|---|---|---|
| 4,017,188 | 4/1977 | Sawatari | 356/376 |
| 4,088,408 | 5/1978 | Burcher et al. | 356/376 |
| 4,091,274 | 5/1978 | Angelbeck et al. | 250/201 |
| 4,183,672 | 1/1980 | Raber et al. | 356/376 |
| 4,332,477 | 6/1982 | Sato | 356/376 |
| 4,534,650 | 8/1985 | Clerget et al. | 356/376 |

Primary Examiner—F. L. Evans
Attorney, Agent, or Firm—Ellsworth R. Roston; Charles H. Schwartz

[57] ABSTRACT

This invention enables examination of semi-conductor chips either on a planar basis or on a three-dimensional basis to determine the characteristics of the chips. Laser light is passed through a first pinhole and is focussed on a wafer. The light reflected from the wafer is passed through a second pinhole and is focussed on a photo-multiplier. The focal length between the first pinhole and the wafer is the same as the focal length between the second pinhole and the multiplier. This arrangement provides for a high signal-to-noise ratio to be produced and image information data to be provided within minimal time lags such as a small fraction of a second. An electrically controllable active mirror operable within the beam-shaping optics of the scanning field may be included to displace the plane of the examination field. This active mirror may be controlled to assume the shape of different types of mirrors including a planar mirror. By controlling the operation of the active mirror, the etchings of first materials on the wafer and the depositions of other materials on the wafer may be examined at different depths. The control of the active mirror may be provided at a different frequency than the frequency of the light providing for the examination of the wafer. The visual portion of the light spectrum from the laser may be further processed to determine such parameters in the wafer as the distribution of photoresist residues on the wafer.

24 Claims, 3 Drawing Figures

APPARATUS FOR, AND METHODS OF, DETERMINING THE CHARACTERISTICS OF SEMI-CONDUCTOR WAFERS

This invention relates to apparatus for operating on semi-conductor wafers to determine the characteristics of the wafers and particularly to determine if the wafers have been constructed properly. The invention also relates to methods of determining the characteristics of the wafers. The invention is not only effective in determining the characteristics of the completed wafers but also in determining the characteristics of the wafers at progressive stages of fabrication.

As semi-conductor technology advances, the size of the semi-conductor chips becomes progressively reduced. For example, the heart of a microcomputer can now be provided on a semi-contuctor chip which is no larger than ¼ inch by ¼ inch. In this space, hundreds and even thousands of circuits are provided. As will be appreciated, the circuits are quite small. For example, the thickness of the circuits may be in the order of a few microns.

Since the circuits on the semi-conductor chips are so small, they have to be quite precise. For example, if the thickness of the circuits varies, the resistance of the circuits varies. Furthermore, variations in the thickness of the circuits affects the spacings between adjacent circuits. This affects the distributed capacitances between adjacent circuits. As a result, the performance characteristics of the circuits vary. Although the above discussion relates to the thickness of the circuits, variations can also occur in the depths of the circuits. These variations also affect the parameters of the circuits.

As will be seen, it is important to provide equipment which will have a measurement sensitivity at least matching the precision required for the fabrication of the circuits on the semi-conductor chips. A considerable effort has been made, and a substantial amount of money has been expended, to provide such measuring equipment. In spite of such effort and expenditure of money, the equipment now in use is not as sensitive, precise or reliable as may otherwise be desired. For example, the measuring equipment now in use does not measure the thickness or depth of individual layers on the chip, or of the resultant circuits, with a precision which will provide an optimum aid to fabricators of semi-conductor chips.

This invention enables examination of semi-conductor chips either on a planar basis or on a three-dimensional basis to determine the characteristics of the chips. In one embodiment of the invention, laser light is passed through a first pinhole and is focussed on a wafer. The light reflected from the wafer is passed through a second pinhole and is focussed on a photomultiplier. The focal length between the first pinhole and the wafer is the same as the focal length between the second pinhole and the multiplier. This arrangement provides for a high signal-to-noise ratio to be produced and image information data to be provided within minimal time lags such as a small fraction of a second.

An electrically controllable active mirror operable within the beam-shaping optics of the scanning field may be included to displace the plane of the examination field. This active mirror may be controlled to assume the shape of different types of mirrors incuding a planar mirror. By controlling the operation of the active mirror, the etchings of first materials on the wafer and the depositions of other materials on the wafer may be examined at different depths. The control of the active mirror may be provided at a different frequency than the frequency of the light providing for the examination of the wafer. The visual portion of the light spectrum from the laser may be further processed to determine such parameters in the wafer as the distribution of photoresist residues on the wafer.

In the apparatus of this invention, the confocal arrangement of the first pinhole with respect to the focal plane of a microscope objective focuses the scanning laser light bundle on the examination field. A favorably high signal-to-noise ratio is obtained and, therefore, image information data desirable for a reliable diagnosis may be obtained within minimal time intervals e.g. within small fractions of a second to at most a few seconds. The intensity of the scanning light may be enhanced, when desired, to obtain high-contrast pictorial representations of the examination object.

The use of the microscope objective for focusing the scanning light bundle in the apparatus of this invention enables a narrow limitation to be provided in the depth of the examination field. By including the electrically controllable active mirror to operate within the beam-shaping optics of the scanning optical path, the plane of the examination field may easily be displaced with respect to a median position. This median position is correlated with the operation of the active mirror. This active mirror may be controlled to operate as different types of mirrors including a planar mirror. Therefore, a high-resolution subdivision of an examination object into a plurality of thin layer-shaped examination fields may be displayed by the apparatus of this invention for a comparative inspection.

The apparatus of this invention provides for the storage of image data for a plurality of equidistantly spaced examination fields, respectively, which may be planar and may be separated from one another in step-widths of 1 $\mu$m to 10 $\mu$m. Such data can be processed by an appropriate computer-controlled display unit and displayed by the unit as representations of the examination object along arbitrarily oriented and/or shaped sectional planes or curved areas. By providing sufficiently small step-widths from examination plane to examination plane and storing the images in such examination planes in an image memory having a sufficiently high storage capacity, the stored image data may be processed in a data processing system to provide a sharp 3D-image of the examination object as seen from arbitrary directions and in any sectional representations.

An additional scanning apparatus may be included in the invention and may be operated at a lower scanning frequency than the main scanning apparatus used to generate the image data characteristics of the examination object. By using such additional scanning apparatus, a point-spread function may be detected for a selected number of image spots within the examination or image field. The point-spread-function describes the spatial intensity distribution for light which is redirected from the image spot into the optical path used for detection.

By proper analysis of the point-spread-function, structures of an image-element smaller than the wavelength of the scanning light may be detected. By comparing the detected, i.e. real, point-spread-function with an ideal point-spread-function as defined by the geometrical-optical boundary conditions, error signals may be generated which may be used to control the active mirror in such a manner that precise indications of the etchings, or the depositions, on the semi-conductor chips may be obtained. The effect is, so to speak, a "smoothing" of the focal plane of the microscope objective within the scanning optical path.

This application corresponds to application Ser. No. P34 22 143.3 filed by applicant in the Federal Republic of Germany on June 14, 1984. Applicant accordingly claims the benefit of the Convention date of June 14, 1984. Furthermore, the apparatus disclosed and claimed in this application is similar in many respects to the apparatus disclosed and claimed by me in application Ser. No. 706,619 filed by me in the United States Patent Office on Feb. 28, 1985.

Figure 1:
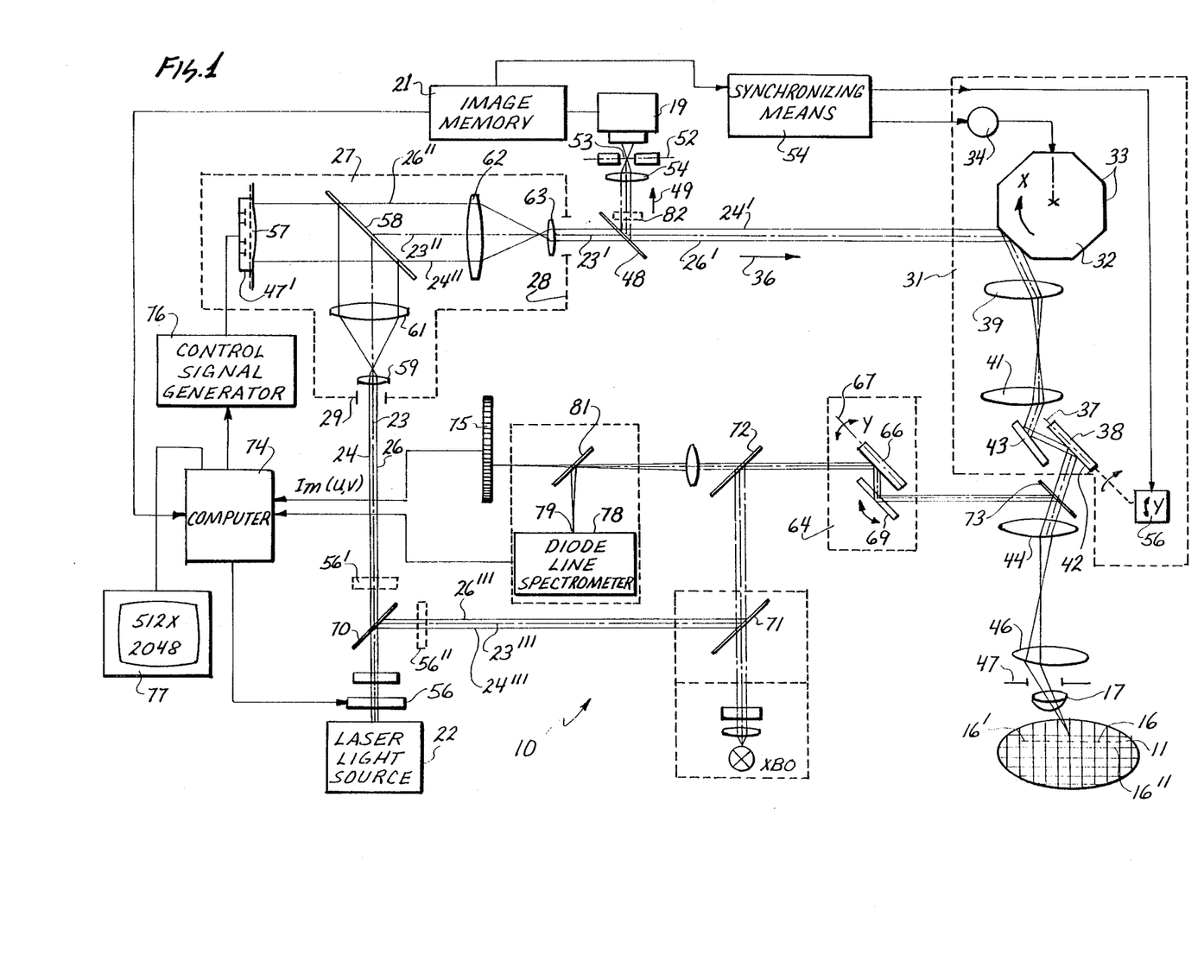
FIG. 1 is a diagrammatic representation of the apparatus of this invention and shows in detail scanning and processing members for producing an optical path to generate a pictorial representation of the etchings or depositions on a semi-conductor wafer.

Referring to FIG. 1, apparatus generally shown at 10 according to the invention is shown which is particularly intended to inspect, or determine the characteristics of, a wafer 11. The apparatus 10 of this invention is capable of inspecting, or determining the characteristics of, depositions on the surface of the wafer or etchings in the wafer. The apparatus 10 is further capable of inspecting, or determining the characteristics of, such wafers 11 at intermediate or final stages of fabrication. The apparatus 10 is particularly adapted to be used to provide quality control in the fabrication of the wafers. In the following description of structural and functional properties of the apparatus 10, methods for its appropriate use will be explained. These methods constitute a substantial aspect of the invention.

Each wafer 11 may constitute a base plate made from a suitable material such as silicon to provide electrical insulation and a support for the layers of material deposited on the plate. The wafer is generally cylindrical and has one (1) flat side. The plate may have any suitable diameter such as a diameter to approximately six inches (6"). Electrical circuits are deposited on the wafer 11 such as by well known techniques of etching, evaporization, oxidation and implantation. The apparatus 10 inspects the wafers 11 after progressive steps and compares the wafers with pre-defined structures and characteristics to recognize manufacturing defects and to eliminate these defects before any further steps of fabrication or to remove the wafers before any such further steps.

In its basic structure, the apparatus 10 is a laser-scan-microscope which, in basic analogy to the generation of a television picture, is providing for a line-by-line scanning. Within each scanning line, the apparatus 10 provides for a point-by-point scanning of an examination field 16. The examination field 16 is schematically represented in FIG. 1 by the focal plane of a microscope objective 17. This focal plane is illustratively assumed to be a plane within or on the wafer 11. Preferably this focal plane is assumed to be the surface generated on the wafer structure after certain procedural steps in the fabrication of the wafer.

In providing this line-by-line and point-by-point scanning, individual field elements (or points) of the examination field 16 are sequentially illuminated with laser-light as by a light source 22. The light source 22 may be a helium-cadmium laser which emits light preferably at wavelengths in the near ultraviolet-spectral range and in the violet range of the visible spectrum. Such wavelengths may be illustratively at $\lambda 1 = 325$ nanometers and $\lambda 2 = 440$ nanometers.

The light illuminating the individual field elements is reflected or scattered from the individual field elements in synchronism with the light-scanning of the examination field. The intensity of the laser light reflected or scattered from the examination field is detected by a photoelectric detector such as a photomultiplier 19. The light detected by the photomultiplier 19 may be introduced, in the form of signals, to an image memory 21 and stored in the image memory 21 for further processing. For example, the information stored in the image memory 21 may be used for image generation and/or computational processing.

The laser constituting the light source 22 may be a continuous wave laser which is continuously light-emitting. In FIG. 1, the primary light bundle of this He-Cd laser is represented by a dash-dotted central beam 23 and by marginal beams 24 and 26. The primary light bundle 23, 24 and 26 from the He-Cd laser 22 is a substantially parallel bundle having a cross-section of about one (1) square millimeter (1 mm$^2$).

The laser-light bundle may be shaped by beam-shaping optics generally indicated in broken lines at 27. By such shaping, the output light bundle emerging from the beam-shaping optics 27 and defined by marginal beams 24' and 26' has a larger cross section than the light bundle has at an input 29 of the beam shaping optics 27. As a result, an appropriate adjustment is made in the bundle cross section to facilitate optical arrangements and to provide for optical processing, and appropriate adjustment, in the convergence of the laser-light bundle to an object to be described hereinafter in some more detail. The output light bundle emerging from the beam shaping optics 27 is indicated at 23', 24' and 26' and the light bundle in the light-shaping optics 27 is indicated at 23", 24" and 26".

The output light bundle 23', 24' and 26' is directed to a first scanning sub-assembly shown in broken lines and indicated generally at 31. The scanning sub-assembly 31 provides for horizontal and vertical deflections of the beam. These beam deflections enable scanning of an examination field 16 in an X-coordinate direction and a Y-coordinate direction. As a horizontally deflecting element in the scanning sub-assembly 31, a polygonal mirror 32 is provided with facets such as shown in FIG. 1. These facets may define an octagon having eight (8) equal sides. In a typical form, however, the polygonal mirror 32 may have as many as 25 facets in an equilateral polygonal relationship. The polygonal mirror 32 may be rotated by a motor 34.

The polygonal mirror 32 is driven rotationally. The rotational frequency of the polygon mirror 32 is synchronized with the input into the photomultiplier 19 of the data relating to the light intensity. This synchronization occurs in the image memory 21, in which the image of the examination field 16 is stored in digital format.

Seen in the direction of an arrow 36 corresponding to the direction of propagation of the laser-light bundle 23', 24' and 26', the Y-deflection member is arranged subsequent to the X-deflection members 32 and 34. The Y-deflection element may constitute a pivotably driven galvanometer mirror 38 which is pivotable relative to a horizontal axis 37.

By means of a telecentric optical path which comprises two lenses 39 and 41 in a suitable arangement such as a 4-f-arrangement (f=the focal length of each of the lenses 39 and 41), the light directed to the facets 33 of the polygonal mirror 32 is imaged on the reflecting surface of the galvanometer mirror 38. A deflecting mirror 43 is disposed between the galvanometer mirror 38 and the exit lens 41 of the telecentric optical path defined by the lenses 39 and 41. The deflecting mirror 43 is provided to obtain an appropriate and accurate geometry of the optical path.

A telecentric arrangement defined by lenses 44 and 46 is analogous to the telecentric arrangement defined by the lenses 39 and 41. The telecentric arrangement defined by the lenses 44 and 46 provides for the imaging of the reflecting surface 42 of the galvanometer mirror 38 on an entrance pupil 47 of the microscope objective 17. The microscope objective 17 focuses onto the examination plane 16, as a parallel or substantially parallel bundle, the laser light passing through the entrance pupil 47.

Any laser light reflected and/or scattered by any inhomogenities in the focusing or examination field plane 16 is redirected into the scanning optical path in a direction indicated by an arrow 49. The light reflected in the direction 49 is in the form of a light bundle 23', 24' and 26'. This light bundle is reflected by a partially transparent mirror 48 disposed between the polygonal mirror 32 and the beam shaping optics 27 and is focussed by a further microscope objective 54. A pinhole 53 is disposed in the focal plane 52 of the microscope objective 54. The pinhole 53 limits the light bundle so that the only light passing through the pinhole 53 is that which emerges from a portion of the examination field corresponding to the depth of focus of the microscope objective 17. The light passing through the pinhole 53 is used for intensity measurements.

The photomultiplier 19 is disposed behind the pinhole in the direction 49 in which the light in the bundle 23', 24' and 26' is propagated. The photomultiplier 19 generates an output signal in proportion to the intensity of the laser-light which is redirected (reflected and/or scattered) from the examination field 16 into the scanning optical path.

The generation of the output signals by the photomultiplier 19 is controlled by a synchronizing means 54 which controls the rotation of the polygonal mirror 32 and the pivotal movements of the galvanometer mirror 38, the latter with the help of a pivot drive 56. The output signals generated by the photomultiplier 19 for each of the point-shaped elementary parts of the examination field 16 are stored in the image memory 21.

The examination field 16 may be displayed by a television monitor to generate an image representative of the examination field 16. For example, the examination field may be subdivided such as into 512×2048 elementary image points. In accordance therewith, 512 lines are scanned, and within each line 2048 image points are scanned. This is analogous to the generation of a normal television picture in Europe. Although a different number of lines are stored in the United States, the generation of such a number of lines is within the scope of this invention.

The size, i.e. the dimensions, of the elementary image points in the "horizontal" and "vertical" directions then results from a horizontal extension of the examination field 16 divided by the number of elementary image points in each line, and from a "height" of the examination field divided by the number of lines in the field. The size of the examination field 16 may be variable between 100 $\mu$m (micrometers) and several mm (millimeters) in accordance with the focal length of the microscope 17. Consistent therewith, the size of the elementary image points may be variable between 0.05 $\mu$m and several $\mu$m.

Scanning of the examination field 16 occurs so fast that the image area is scanned within 40 ms (milliseconds), every 20 ms (milliseconds) a half-image being generated. One of these half images is formed from the even lines and the other half image is from the odd lines. These half images are interlined in a manner which is well known in the art.

The storage of the output signal from the photomultiplier 19 in synchronism with the scanning movements of the polygonal mirror 32 and the galvanometer mirror 38 is achieved in a manner well known in the art. This is described in a scientific publication in 1979 by Shack et al (R. Shack, R. Baker, R. Buchroeder, D. Hillmann, R. Shoemaker and P. H. Bartels), in the Journal of Histochemistry and Cytochemistry at Vol 27, page 153.

An electro-optical or an acousto-optical modulator 56 is also synchronized with the read-in frequency of the image memory 21. The modulator controls the intensity with which the scanning light beam is directed to the examination field 16. Thereby, selected portions of the examination field 16 may be illuminated with a greater light intensity than other portions of the field. This is particularly important in applications where selected portions of the examination field are imaged with high contrast, but where the average light exposure of the examination object is to be maintained as low as possible.

To provide for the capability of scanning a plurality of spaced examination fields or planes 16, 16' and 16" in a short time sequence, an active mirror 57 is provided. By an electrical control, a positive or negative refractive power can be imparted to the mirror 57 to enable an adjustment in the position of the examination plane 16. This adjustment may be within a range of 10 $\mu$m relative to a preselected position of the examination plane 16 as seen in a direction perpendicular to the plane 16. If no control signal is applied to the active mirror 16, the mirror acts as a planar mirror.

The active mirror 57 is disposed in a pupil plane 47' which corresponds optically to the plane of the entrance pupil 47 of the microscope objective 17. The mirror 57 is illuminated by a partially transparent—normally, a semi-transparent mirror 58 which is included in the beam-shaping optics 27. The mirror 58 receives the laser output light bundle 23, 24 and 26, after the light bundle has been widened in its cross section through the action of the arrangement defined by the telecentric lenses 59 and 61. The lenses 59 and 61 may be convex lenses of different focal lengths.

After reflection at the active mirror 57 and transmission through the partially transparent mirror 58, the light bundle represented in FIG. 1 by the margin-defining beams 26" and 24" passes a second telecentric arrangement of lenses 62 and 63 included in the beam shaping optics 27. As a result, the cross section of the light bundle 23', 24' and 26' emerging through the aperture 28 at the exit of the beam-shaping optics 27 is adjusted to a size appropriate for the processing of the laser light bundle within the first scanning apparatus 31.

By appropriate control of the active mirror 57, the apparatus 10 may be rapidly and precisely adapted to scan different examination fields such as the equidistantly spaced examination fields 16, 16' and 16". With a sufficient storage capacity in the image-memory 21, the total yield of the image data obtained from a scanning of all of the different examination fields may be stored in the image memory 21. The contents of the image memory 21 may then be processed to generate pictorial representations of the examination object along arbitrary sectional planes which may be perpendicular, parallel or inclined with respect to the scanned examination fields such as the examination fields 16, 16' and 16".

When scanning the different examination fields such as the examination fields 16, 16', and 16" as described in the previous paragraphs, the pictorial representations obtained may be burdened with minor blurs. These blurs may arise from the circumstance that light adjacent the examination fields 16, 16' and 16" may contribute to the intensity distribution of the laser light which is detected by the photomultiplier 19. Successive scanning of the progressive examination fields 16, 16' and 16", however, offers the opportunity to reliably recognize aberrations in such pictorial representations so that light from other planes than the focal plane 16 are rejected and only light from the focal plane 16 remains.

By processing, in the image memory 21 and the data processor 74, the contents representing the different examination fields, such as the fields 16, 16' and 16", sharp and high-contrast pictorial representations of the inspected structures may be obtained. This may be achieved by proper use of the 3-dimensional transfer function of the microscope objective 17. This 3-dimensional transfer function is well known in the art. Since the computational correction of the picture quality can be provided with respect to any of the examination planes 16, 16' and 16", pictorial representations can be generated with a quality as if the depth of focus of the microscope objective 17 were infinite. These pictorial representations can include cutting profiles of the depositions provided on the wafer 11 such as etched photoresist structures, conductive metal structures and insulating silicon oxide (SiO ) structures.

As described above, a characteristic feature of the apparatus 10 is the confocal arrangement of the pinhole 53 relative to the focal plane of the microscope objective 17. This focal plane corresponds to the examination field 16. This arrangement is instrumental in insuring that the light passing through the pinhole 53 has the same depth of focus as an image generated by the microscope objective 17. Because of the confocal arrangement of the pinhole 53 relative to the image generated by the microscope objective 17, light reflected from parts of the examination object disposed in front of, or to the rear of, the examination field (when viewed in the direction of propagation of the laser light) is directed to the walls defining the pinhole 53. Such light is thereby prevented from contributing to the intensity of the output signal produced by the photomultiplier 19. This is of particular importance in view of the fact that the thickness of the examination field 16 corresponding to the region defining the depth of focus of the microscope objective 17 is quite small. For example, it may vary in typical cases between approximately 0.05 μm and 1.0 μm.

In a typical dimensional layout of the apparatus 10, the microscope objective 17 has a focal length of approximately five millimeters (5 mm) and a numerical aperture of 0.9 and the diameter of the laser-light bundle 23, 24 and 26 focused by the microscope objective 17 on the examination field 16 has a value to approximately six millimeters (6 mm). With a proper choice of the microscope objective 17 and of the cross-sectional area of the light bundle, a resolution of less than 0.2 μm may be achieved.

As a result of inhomogenities or irregularities in a layer or part of the examination object through which the scanning light is transmitted before it is focused onto the examination field 16, the focal plane (which, by tacit implication, has been assumed to be a flat and smooth plane) may be deformed as a result of aberrative effects. Such image distortions may result in at least partially blurred images. To compensate for such deformations in the focal plane, a scanning sub-assembly shown in broken lines and generally indicated at 64 is provided. The scanning sub-assembly 64 functions in the same manner as described above for the scanning sub-assembly 31 and enables a partial or complete scanning of the examination field 16.

The apparatus 64 includes as its scanning elements first and second galvanometer mirrors 66 and 69. The first galvanometer mirror 66 is pivotable about a horizontal axis 67 parallel to the plane of propagation of the scanning light. The galvanometer mirror 66 provides for a Y-deflection of the scanning light. The galvanometer mirror 69 is pivotable about an axis which extends perpendicular to the plane of propagation of the scanning light. The galvanometer mirror 69 provides for an X-deflection i.e. the line-deflection of the scanning light.

The light provided within the scanning sub-assembly 64 for scanning the examination object is a partial light bundle 23''', 24''' and 26'''. This light bundle is branched from the primary light bundle 23, 24 and 26 of the laser 22 by a beam splitter 70, such as a partially transparent mirror. As shown in FIG. 1, the partial light beam 23''', 24''' and 26''' is deflected by a first partially transparent mirror 71 to a second partially transparent mirror 72 and is directed from the mirror 72 into the scanning apparatus 64. The light beam 23''', 24''' and 26''' then passes to a third partially transparent mirror 73 after being processed by the scanning sub-assembly 64.

The partially transparent mirror 72 is disposed between the galvanometer mirror 38 in the scanning apparatus 31 and the telecentric arrangement defined by the lenses arrangement 44 and 46. The partially transparent mirror 73 is disposed between the scanning apparatus 31 and the entrance pupil 47 of the microscope objective 17. The intensity of the partial light beam 23''', 24''' and 26''' is only about ten percent (10%) of the intensity of the primary light beam 23, 24 and 26 from the laser 22. The light beam from the partially transparent mirror 73 is coupled into the optical path for imaging the examination field 16. The relative amount of the light passing from the laser 22 to the primary path including the beam shaping optics 27 and the secondary path including the scanning sub-assembly 64 may be respectively provided by modulators 56' and 56".

The operational mode of the scanning sub-assembly 64 is preferably asynchronous with respect to the scanning sub-assembly 31 and the scanning frequency of the scanning sub-assembly 64 is considerably lower than that of the scanning sub-assembly 31. The light reflected and/or scattered at the examination object and thereby redirected into the optical path of the scanning subassembly 64 is detected by a 2D-matrix-array of photoelectric detectors, preferably a diode matrix 75.

In this way, in response to each illumination of an image spot or element of the examination field, a two-dimensional intensity distribution of radiation is redirected (reflected and/or scattered) from the examination field 16 into the optical path of the scanning subassembly 64. This two-dimensional intensity distribution or radiation is detected by the diode matrix 73 to provide a point-spread function. This function is stored in the data processor 74 for further processing.

By using well known mathematical algorithms the basic structures of which will be explained, calculations may be made, from the point-spread function, of deviations in the shape of the wavefront of light which has passed through parts of the examination object. These deviations represent variations from an ideal shape of the wavefront which would be normally expected if no examination object were present. Deviations of the point-spread function from an ideal shape may be interpreted by the data processor 74 to indicate that the examination object is affected by untypical aberrations.

The detection of the point-spread function is also of particular interest because it represents aberrations which are even smaller, in the distribution of the spot-image structures, than those of the scanning spot or the scanned elements of the examination field. The information obtained from an evaluation of the point-spread function with respect to the shape of the wavefront of the scanning light may be interpreted to represent a "deformation" in a focal plane of the microscope objective 17. This information may also be used to activate the active mirror 57 to compensate for such deformations.

As a result, the data provided by the scanning sub-assembly 64 and representing the point-spread function may be used to monitor a variable for signals which correct the characteristics of the active mirror 57. These correcting signals may be applied to the active mirror 57 to compensate for the image distortions from which the deformations of the wavefront and the focal plane occur. This compensation is achieved in the direction in which the examination field 16 is being scanned by the scanning sub-assembly 64.

The evaluation of the data representing the point-spread function is provided by the data processor 74. In providing this evaluation, the data processor 74 compares the signals from the diode matrix 73 and signals representing an ideal point-spread function and provides output signals representing any such differences. In response to output signals from the data processor 74, a signal regulator 76 produces control signals to obtain an appropriate compensatory adjustment of the active mirror 57. In this way, the intensity distribution measured by the scanning sub-assembly 64 provides a close approximation of the ideal point-spread function. The data processor 74 is also used as a display control unit which, by an appropriate processing of the intensity data stored in the image memory 21, enables the display of images of the examination object in a desired variety of section planes.

By controlling the point-spread function as described in the previous paragraph, the distance of the focal plane from a reference plane such as the plane 16 can be controlled. As a result, the thickness of the deposition layers on the wafer 11 or the heights of etched surfaces may be precisely measured. This means that the surface structures of the wafer 11 can be represented in the three co-ordinate directions constituting the X, Y and Z directions.

Figure 2:
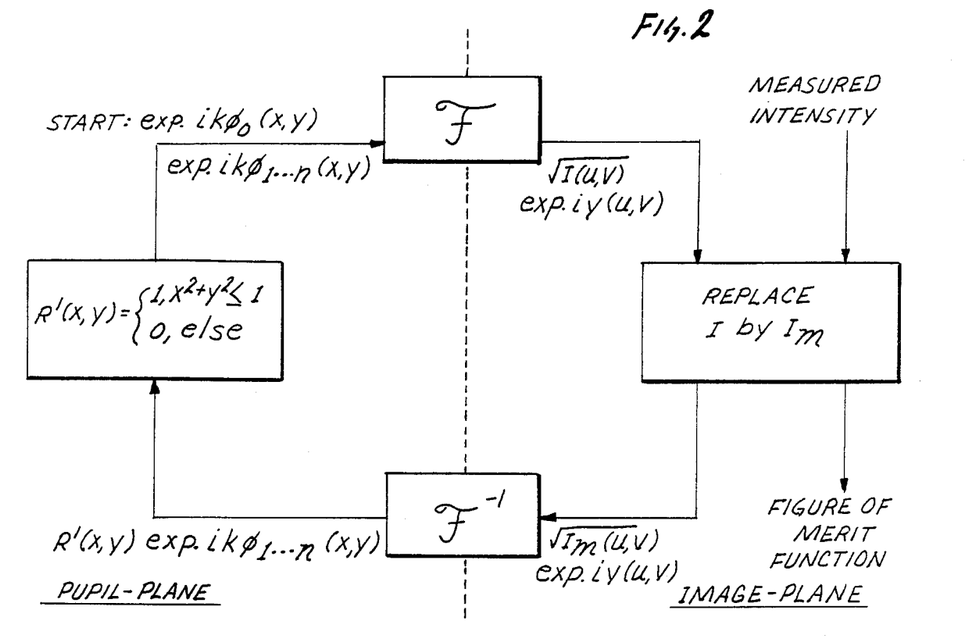
FIG. 2 is a schematic representation of apparatus for providing mathematical analyses to evaluate point-spread-functions and to generate correction signals, in accordance with such analyses, for proper adjustment of an active mirror used to compensate image distortions in the apparatus shown in FIG. 1.

Reference is now made to FIG. 2, which is a schematic representation of a computational procedure for processing in the data processor 74 the data relating to the point-spread function. This procedure basically consists in producing an iteration in which the intensity distribution (of the point-spread function) Im (u, v) (u=line index, v=column index of the diode matrix 75) is used to calculate, for the plane of the entrance pupil 47 of the microscope objective 17, a shape of the wavefront of the scanning light. This shape is consistent with the detected intensity distribution Im (u, v). As a reasonable initial condition, no deformation occurs in the focal plane and the radiation field at the location (x, y) of the entrance pupil 47 of the microscope objective 17 has a plane wavefront which is characterized by a phase factor $\phi(x, y)$.

The transfer function of the optical system includes a typical structure of that part of the examination object to which the scanning light beam passes, i.e. the light distribution in the image plane is derived by a convolution of the wavefront $R(x,y) \cdot \exp ik\ \phi(x,y)$ with the transfer function. In consideration of such transfer function, the shape of the radiation (light)-field $\sqrt{I(u,v)} \exp i\gamma(u,v)$ in the focal plane of the microscope objective 17 is calculated. The amplitude factors $\sqrt{I(u,v)}$ may be replaced by the values $\sqrt{Im(u,v)}$. Such values may be obtained from the intensity measurements and from the application of the inverse transfer function $F^{-1}$ to the shape of the radiation light-field in the focal plane of the microscope objective 17. By replacing the amplitude factors $\sqrt{I(u, v)}$ by the values $\sqrt{Im(u,v)}$, a shape of the wavefront at the entrance pupil 47 of the microscope objective 17 is calculated which is consistent with the set-up field-shape. This shape has a phase factor $\phi_1(x, y)$ consistent with the set-up field-shape.

In a first iteration step, the phase factor $\phi_1(x, y)$ is set up for a mathematical description of the radiation field at the location of the entrance pupil 47. The radiation field in the focal plane of the microscope objective 17 is again calculated. As a result, the amplitude-factors are replaced by the square-roots of the measured intensities and a new phase factor $\phi_2(x, y)$ is calculated. Such iteration steps are repeated until the measured intensities agree within tolerable limits with the calculated intensity values. In this way, a wavefront at the position of the entrance pupil 47 of the microscope objective 17 is determined. This wavefront is consistent with the measured intensity values.

By comparing the wavefront shapes resulting from the interation procedure, the wavefront at the entrance pupil of the microscope objective 17 for an ideal case with control signals can be generated, through the operation of the data processor 74 and the regulator 76, for adjusting the active mirror 57. The active mirror 57 is adjusted to make the measured intensity distribution Im (x, y) substantially identical with an ideal intensity distribution in the focal plane of the microscope objective 17. This ideal distribution would result if the radiation field wavefront at the entrance pupil 47 of the microscope objective 17 were ideal.

In this way, the transfer function of the optical system can be adjusted to smooth the focal plane 16 of the microscope objective 17 and to insure that the image information from the scanning sub-assembly 31 corresponds to that which would be obtained under ideal imaging conditions. In other words, the transfer function of the optical system is adjusted to achieve a realistic image of the examination field 16.

In the apparatus 10, further provision is made to couple white light, with a broad-band spectral distribution, into the optical path of the scanning sub-assembly 64. A xenon-high pressure lamp XBO is preferably used as the source of the white light. This provides for the capability of measuring optical thicknesses of layer structures for selected parts of the examination field 16, in particular those parts of the examination field which are inspected by the "fast" scanning sub-assembly 31. The layer thickness of these structures are detected point by point. Values of detection as high as one thousand (1000) per second can be measured. The measurement of layer thickness is accomplished by using the principles of white-light interferometry to determine the wavelengths of constructive interference. To measure layer thickness, a diode-line spectrometer 78 is provided with an entrance slit 79. The slit 79 receives light passing from the test object and reflected by a partially transparent mirror 81.

Because of the use of the He-Cd-laser 22 as a scanning light source, the apparatus 10 may also be used to record the spatial distribution of luminescent molecules within the inspected parts of an examination object. To accomplish this, a filter 82 may be disposed between the photomultiplier 19 and the partially transparent mirror 48. The filter 82 is transparent for the luminescence radiation from the test object but non-transparent for the luminescence exciting radiation of the laser in the ultra-violet range and the radiation in the violet range.

Figure 3:
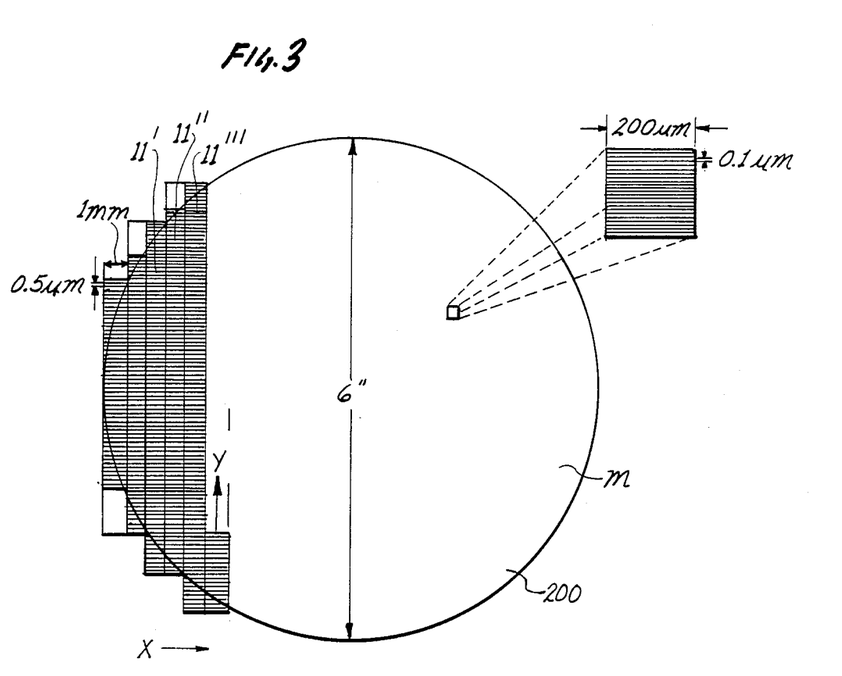
FIG. 3 schematically illustrates a particular apparatus and method of scanning the examination field of a wafer.

An alternate method of scanning the examination field may occur as shown in FIG. 3. As shown in FIG. 3, a table 200 is movable in x- and y-coordinate directions as well as along a line which shows undulatory and/or retangular-undulatory bends. The x-coordinate direction corresponds to the direction in which the polygonal mirror 32 deflects the light beam. In this direction the step-width of each movement of the wafer 11 by the table 200 is equal to the amplitude of the light beam. In the direction of the y-coordinate, the amplitude of each movement of the wafer 11 by the table 200, corresponds to the extension of the selected examination field. As a result, the scanning apparatus processes adjoining parallel stripes such as stripes 11', 11", 11'" upon successive movements of the table 200 in the y-coordinate direction.

The positioning of the light beam as described in the previous paragraph has the advantage of a fixed mirror being used instead of the galvanometer mirror 38 in the scanning sub-assembly 31 in FIG. 1. In addition, a faster scanning of the examined field will be enabled in the embodiment of FIG. 3 than in the embodiment of FIG. 1 since the wafer 11 may continuously be moved in the y-direction. It is obvious that such an x-, y- transport means can also be used in combination with the apparatus 10 shown in FIG. 1, the movement of the transport means being discontinued selectively for scanning small selected areas of the wafer 11.

A quick comparison of an area scanned line-by-line with a pre-defined structure can be provided also with the aid of a so-called convolver. The function of such a convolver is based on a non-linear superimposition of acoustic surface waves, the amplitudes of which are modulated in accordance with the intensity of the distribution of the light reflected on the detector of the scanning apparatus, registered within one scanning line.

In the convolver, acoustic waves are generated in opposite directions. The acoustic waves generated in one direction correspond, in terms of their course of amplitudes, to the pre-defined structure and the acoustic waves generated in the other direction correspond to the measured course of intensity. If these surface waves propagating in the opposite directions display the same amplitudes, the correlation function resulting from a non-linear super-position of such acoustic waves has a maximum value. In this context, the magnitude of the correlation function may be measured as a voltage on a piezoelectric material at a cover electrode of the convolver. The value of the correlation function of the two surface waves obtained in this manner thus determines the correspondence between the scanned structure and the pre-defined structure. Such a convolver may not only be used for recognizing structural defects but also for autofocussing the beam from the scanning sub-assembly 31 onto the surface of the wafer 11.

Although this invention has been disclosed and illustrated with reference to particular embodiments, the principles involved are susceptible for use in numerous other embodiments which will be apparent to persons skilled in the art. The invention is, therefore, to be limited only as indicated by the scope of the appended claims.

We claim:

1. A method of determining the characteristics of electrical circuitry on a semi-conductor wafer, including the steps of:
   providing a light beam,
   focussing the light beam at an entrance pupil,
   positioning the semi-conductor wafer at a particular focal distance from the entrance pupil for reflection of the light beam by the semi-conductor wafer,
   passing the reflected light beam through a pinhole,
   focussing the reflected light beam at the pinhole, and
   positioning a light sensor at the particular distance from the pinhole to obtain the production of signals by the light sensor in accordance with the characteristics of the light sensed by the sensor.

2. A method as set forth in claim 1, including the steps of:
   adjusting the relative distance of travel of the light beam to the entrance pupil at individual planar positions in the light beam to provide sharp indications of the etchings and the depositions on the semi-conductor wafer.

3. A method as set forth in claim 1 including,
   wherein the method provides for an examination of the electrical circuitry on the wafer in a particular examination field and wherein
   the examination field of the electrical circuitry on the semi-conductor wafer is adjusted incrementally to provide an indication of the characteristics of the electrical circuitry on the semi-conductor wafer on a three-dimensional basis.

4. A method as set forth in claim 1, including,
   providing a passage of a particular portion of the light beam through the entrance pupil to the electrical circuitry on the semi-conductor wafer,
   directing to a second sensor the light reflected from the passage of the particular portion of the light beam to the semi-conductor wafer to obtain the production of signals by the second sensor in accordance with the characteristics of such reflected light, and adjusting the relative distance of travel of the light beam directed to the first light sensor at different planar positions of the light beam in accordance with the characteristics of the signals produced by the second light sensor.

5. A method of inspecting electrical circuitry on a semi-conductor wafer, including the steps of:

directing a beam of light through an entrance pupil to a particular examination field on the semi-conductor wafer for reflection of the light beam by the semi-conductor wafer, focussing the beam of light at the entrance pupil, the examination field on the semi-conductor wafer being displaced a particular distance from the entrance pupil, directing the reflected beam of light through a pinhole to a light sensor to obtain the production of signals in the sensor in accordance with the characteristics of the reflected light beam, focussing the reflected beam of light at the pinhole, the light sensor being displaced by the particular focal distance from the pinhole, providing a scanning of the beam relative to the wafer in a pair of co-ordinate directions in the examination field on the semi-conductor wafer, and processing the signals produced in the sensor during the scanning of the beam to determine the characteristics of the electrical circuitry on the wafer at the different positions in the examination field on the wafer.

6. A method as set forth in claim 5, including the step of:

eliminating the effects of light reflected from the wafer at different examination fields than the examination field in the electrical circuitry on the semiconductor wafer.

7. A method as set forth in claim 5, including the step of:

providing progressive adjustments in the examination field being examined in the electrical circuitry on the semi-conductor wafer.

8. A method as set forth in claim 6, including the steps of:

providing an active mirror adjustable at individual positions, and adjusting the active mirror at the individual positions to examine only the characteristics of the electrical circuitry in the examination field on the semi-conductor wafer.

9. A method of determining the characteristics of electrical circuitry on a semi-conductor wafer, including the steps of:

providing a first light beam at a first frequency, directing the first light beam to an active mirror for reflection of the beam by the mirror, focussing the reflected beam at an entrance pupil, directing the focussed beam to a particular examination field in the electrical circuitry on the semi-conductor wafer for reflection of the beam from the wafer, the examination plane being displaced by a particular distance from the entrance pupil, focussing at a pinhole the light beam reflected by the semi-conductor wafer, directing to a first light sensor the light beam passing through the pinhole, the first light sensor being displaced by the particular distance from the pinhole, producing a scanning of the first light beam at the different positions in the examination field on the semi-conductor wafer at a first frequency, directing the second beam through the entrance pupil to the semi-conductor wafer for reflection of the second beam from the wafer, producing a scanning of the second light beam at the different positions in the examination field on the semi-conductor wafer at a second frequency different from the first frequency, directing the reflected second beam to a second light sensor, processing the signals produced by the second light sensor, and adjusting the characteristics of the active mirror at individual positions in the mirror in accordance with the signals processed from the second light sensor for corresponding positions in the electrical circuitry on the semi-conductor wafer.

10. A method as set forth in claim 9, including the step of:

processing the signals from the first light sensor to indicate the characteristics of the electrical circuitry in the examination field on the semi-conductor wafer.

11. A method as set forth in claim 9 wherein the characteristics of the active mirror are adjusted to focus the first light beam in examination fields at different depths in the electrical circuitry on the semi-conductor wafer.

12. A method of determining the characteristics of electrical circuitry in a semi-conductor wafer, including the steps of:

providing a first light beam, directing the first light beam to an active mirror for reflection of the beam by the mirror, focussing the first light beam at an entrance pupil, directing the reflected beam to a particular examination field in the electrical circuitry on the semi-conductor wafer for reflection of the beam by the wafer, the particular examination field being displaced by a particular distance from the entrance pupil, focussing at a pinhole the light beam reflected from the examination field of the semi-conductor wafer, directing the focussed light to a light sensor dispalced by the particular distance from the pinhole, scanning the first light beam at a first particular frequency in the examination field of the electrical circuitry on the semi-conductor wafer, providing a second light beam, directing the second light beam through the entrance pupil to the examination field of the electrical circuitry on the semi-conductor wafer, scanning the second light beam in the examination field of the electrical circuitry on the semi-conductor wafer at a second frequency different from the first frequency, sensing the reflected second light beam to produce signals in accordance with such sensing, processing the sensed signals produced by the second light beam, and adjusting the characteristics of the active mirror to adjust the examination by the first beam of different examination fields of the electrical circuitry on the semi-conductor wafer.

13. A method as set forth in claim 12, including the steps of:
    adjusting the characteristics of the active mirror to minimize aberrations in the sensed signals resulting from blurs in the image of the light reflected from the examination field of the electrical circuitry on the semi-conductor wafer.

14. A method as set forth in claim 13, including the step of:
    modulating the first light beam at selected positions during the scan to enhance the intensity of the light directed to the semi-conductor wafer at such selected positions.

15. A method of determining the characteristics of electrical circuitry on a semi-conductor wafer, including the steps of:
    providing a first beam,
    disposing the semi-conductor wafer at a first depth of focus relative to the beam to obtain a reflection of the first beam from the semi-conductor wafer,
    disposing a sensor at the first depth of focus relative to the reflected beam to produce signals in accordance with the characteristics of the reflected beam,
    producing a scan of the semi-conductor wafer by the first beam in first and second co-ordinate directions at a first frequency,
    providing a second beam with different characteristics than the first beam,
    focussing the second beam at the same position on the semi-conductor wafer as the first beam for reflection by the semi-conductor wafer,
    producing a scan of the second beam in the first and second coordinate directions at a second frequency different from the first frequency,
    sensing the second beam reflected from the semi-conductor wafer, and
    adjusting the first beam at the individual positions of scan in the first and second coordinate directions in accordance with the characteristics of the signals produced at such individual positions of scan by the second beam to eliminate any blurs in the characteristics of the reflected first beam at the first depth of focus.

16. A method as set forth in claim 15, including the step of:
    adjusting the particular depth of focus of the semi-conductor wafer relative to the first beam to determine the characteristics of the semi-conductor wafer at different depths in the wafer.

17. A method as set forth in claim 15 wherein
    the first beam is directed from an active mirror to the semi-conductor wafer and the first beam is provided with the particular focal length after being directed from the active mirror and before reaching the semi-conductor wafer and wherein
    the active mirror is provided with adjustable characteristics at individual positions on the active mirror to adjust the focussing of the first beam on the semi-conductor wafer at such individual positions and wherein
    the sensing of the second beam is processed to produce adjustments in the characteristics of the active mirror at individual positions on the mirror for adjusting the focussing of the first beam on the semi-conductor wafer at such individual positions.

18. A method as set forth in claim 15 wherein
    the first beam examines a particular examination field in the electrical circuitry on the semi-conductor wafer and wherein the active mirror is adjusted to adjust the examination field being examined by the first beam on the semi-conductor wafer.

19. A method as set forth in claim 17 wherein the point-spread function of the electrical circuitry on the semi-conductor wafer is determined from the sensing of the second beam and wherein
    the determined point spread function is compared with an ideal point spread function to indicate any differences in such comparison and wherein
    the differences in the comparison are used to provide an adjustment in the characteristics of the active mirror at individual positions on the mirror to minimize any such differences.

20. A method as set forth in claim 19 wherein
    the semi-conductor wafer is movable in first and second co-ordinate directions to provide for a scanning of the semi-conductor wafer by the first and second beams.

21. A method of determining the characteristics of electrical circuitry in an examination field on a semi-conductor wafer, including the steps of:
    directing a light beam toward the electrical circuitry on the semi-conductor wafer,
    focussing the light beam a particular distance from the semi-conductor wafer,
    providing for the examination of successive positions in the examination field of the electrical circuitry on the semi-conductor wafer and for the reflection of light from these positions,
    focussing the reflected light beam at the particular distance from a photodetector to obtain the production of signals from the successive positions in the examination field of the electrical circuitry on the semi-conductor wafer beam in accordance with the characteristics of the light reflected from these positions,
    producing a point-spread function of the light at the different positions in the examination field on the electrical circuitry of the semi-conductor wafer, and
    adjusting the characteristics of the light beam directed to the semi-condcutor wafer for the different positions in the examination field of the electrical circuitry on the semi-conductor wafer in accordance with the characteristics of the point-spread function at these positions.

22. A method as set forth in claim 21 wherein
    the point-spread function is determined by comparing the point-spread function determined for the different positions in the examination field of the electrical circuitry on the semi-conductor wafer with an ideal point-spread function for such different positions in such examination field and by using the results for such comparison to adjust the characteristics of the light beam directed to the semi-conductor wafer for such different positions in such examination field.

23. A method as set forth in claim 21 wherein
    the adjustments in the characteristics of the light beam at the different positions in the examination field of the electrical circuitry on the semi-conductor wafer are made in the following manner:
    determining at a first frequency the characteristics of the light beam reflected from the different positions in the examination field of the electrical circuitry on the semi-conductor wafer, determining, at a second frequency different from the first frequency, the characteristics of the light beam reflected from the different positions in the examination field of the electrical circuitry on the semi-conductor wafer to obtain the point-spread function of the different positions in the examination field of the electrical circuitry on the semi-conductor wafer, and adjusting the characteristics of the light beam at the first frequency in accordance with the characteristics of the light beam at the second frequency.

24. A method as set forth in claim 21 wherein the characteristics of the light beam are adjusted to impart different examination fields of the electrical circuitry on the semiconductor wafer and the characteristics of the light beam for the different examination fields of the electrical circuitry on the semi-conductor wafer are adjusted at individual positions in such examination fields in accordance with the point-spread functions for such different positions in such examination fields.

* * * * *